United States Patent
Ishikawa et al.

[11] Patent Number: 5,147,319
[45] Date of Patent: Sep. 15, 1992

[54] WINGED NEEDLE

[75] Inventors: Toichi Ishikawa; Hiroyuki Asano, both of Yokohama, Japan

[73] Assignee: Kato Hatsujo Kaisha, Ltd., Kanagawa, Japan

[21] Appl. No.: 714,956

[22] Filed: Jun. 13, 1991

[30] Foreign Application Priority Data

Jan. 17, 1991 [JP] Japan .................. 3-016977

[51] Int. Cl.$^5$ ............................................. A61M 5/32
[52] U.S. Cl. ..................... 604/174; 604/180; 604/192; 604/263
[58] Field of Search ........... 604/177, 180, 192, 193, 604/197, 198, 263, 174, 179

[56] References Cited

U.S. PATENT DOCUMENTS

| | | | |
|---|---|---|---|
| 4,664,259 | 5/1987 | Landis | 604/263 |
| 4,850,976 | 7/1989 | Heinrich et al. | 604/263 |
| 4,909,792 | 3/1990 | Norelli | 604/192 |
| 4,944,731 | 7/1990 | Cole | 604/263 |
| 4,966,591 | 10/1990 | Yuen | 604/263 |
| 5,011,475 | 4/1991 | Olson | 604/263 |
| 5,011,479 | 4/1991 | Le et al. | 604/263 |

*Primary Examiner*—Paul J. Hirsch
*Assistant Examiner*—Michael Lynch
*Attorney, Agent, or Firm*—Nikaido, Marmelstein, Murray & Oram

[57] ABSTRACT

A winged needle with which the needle can be safely exposed and covered. The winged needle comprises a base into which the needle is rooted, wings which can be folded to cover the needle, sheath-portion of the wings which surrounds the needle on all sides when the wings are folded, and a coupling device which couples the wings. This structure enables a user to handle the winged needle from the base side without having his hand face the needle tip, significantly reducing the possibility of puncturing the user's hands.

5 Claims, 3 Drawing Sheets

WINGED NEEDLE

BACKGROUND OF THE INVENTION

1. Field of the Invention

The present invention relates to a winged needle comprising wings which facilitate taping onto a part of the body such as an arm when the needle is inserted into a vessel of the arm.

2. Description of the Related Art

A related winged needle, as shown in FIG. 7, has fixed wings C, C' at both sides of the base B into which the needle is rooted. A sheath D, for covering the needle tip A' and preventing accidental contacts thereof, can be coupled to the base B.

Ironically, this sheath D can cause an accidental contact. A sheath D is coupled to the base B tightly enough to ensure the coupling in transportation or storage. Obviously, a user has to give some effort to pull the needle out, with one hand holding the sheath D and the other the winged needle. The moment the sheath D uncouples from the base B, the user reflexes to stop the action; the hands backlash, and the needle may prick the hand holding the sheath.

Or, after use, the user may also puncture his hand by mistake in replacing the sheath for disposal. In this case, there is a possibility of transmitting AIDS or hepatitis type B virus if the patient is a carrier.

SUMMARY OF THE INVENTION

This invention is to eliminate the problems described above, by providing a winged needle with which a user can safely uncover the needle and replace it in a sheath.

In order to achieve such a purpose, the invention comprises a base into which the needle is rooted, wings which flank both sides of the base in order to fold toward the needle, sheath-portion of the wings which will surround the needle on all sides when the wings fold toward the needle so as to meet each other at the needle, and coupling means which holds the wings together.

The wings function to cover the needle when the wings are folded in and coupled by the coupling means, as well as to facilitate taping onto a part of the body such as an arm when the coupling means is disengaged and the needle is in use. In the course of exposing and covering the needle, the winged needle can be handled from the base side, and a user's hand never has to face the needle tip. Thus this invention has an advantage in that there is little possibility of puncturing one's hands during handling.

DESCRIPTION OF THE PREFERRED EMBODIMENTS

Figure 1:
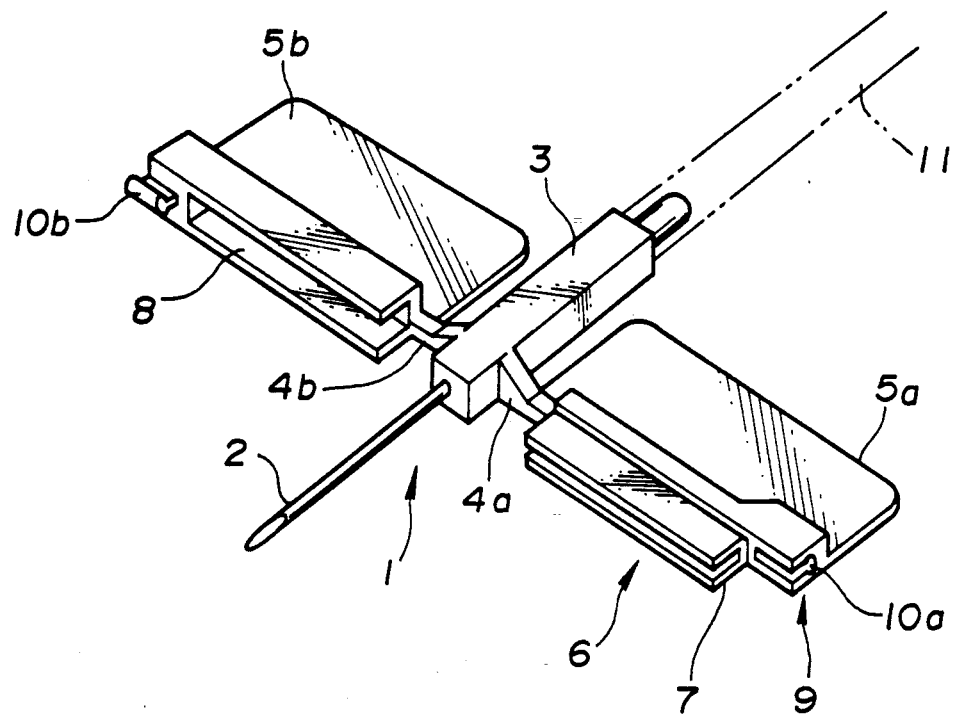
FIG. 1 is a perspective view of the first embodiment of the invention.

Referring to FIG. 1, a winged needle 1 comprises a base 3 into which a needle 2 is rooted, and horizontally opened wings 5a, 5b which, with arms 4a, 4b, flank both sides of the base 3. These elements, base 3, arms 4a, 4b and wings 5a, 5b, are one body made of an elastic material such as synthetic rubber. The wings 5a, 5b can fold, arms 4a, 4b working like hinges, so as to meet each other along the needle 2 as shown in FIG. 2.

Figure 4:
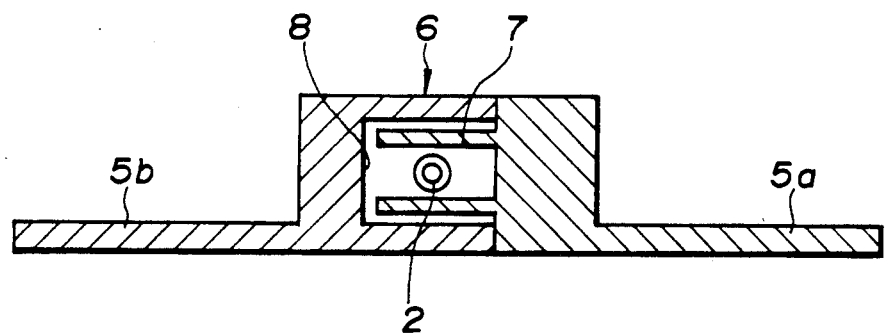
FIG. 4 is an enlarged sectional view of the first embodiment shown in FIG. 3.
Figure 5:
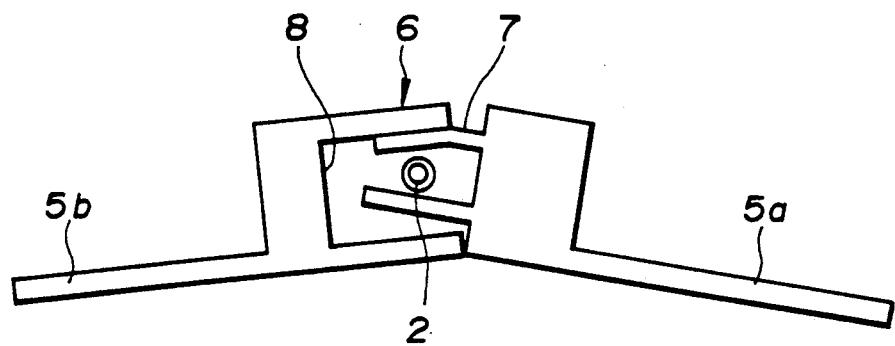
FIG. 5 is an enlarged sectional view of the first embodiment shown in FIG. 3 when there is force applied externally to the wings bending the sheath.

When the wings 5a, 5b fold in to the needle 2, sheath-portion 6 will form a sheath surrounding the needle 2 on all sides. The sheath-portion consists of a ditched projection 7 which is formed along one of the meeting edges of the wings 5a, 5b and of a lipped section 8 formed along the other meeting edge. When the wings 5a, 5b meet in this way, the ditched projection 7 makes a three-sided cover for the needle, and the lipped section 8 embraces the ditched projection 7 to cover the needle on all four sides. Thus the sheath 6 doubly covers the needle 2 as shown in FIG. 4, keeping the needle 2 covered even if there is force applied externally to the wings 5a, 5b bending the sheath along the meeting edges, shown in FIG. 5.

The formation of the sheath or the bend of the arms 4a, 4b is maintained by coupling means 9 which is constituted of a female part 10a and a male part 10b built at the tip of each meeting edge respectively. The female and male parts 10a, 10b couple by elastic deformation. The base 3 is connected to an instillation set (not shown) or the likes through a flexible tube 11.

Figure 2:
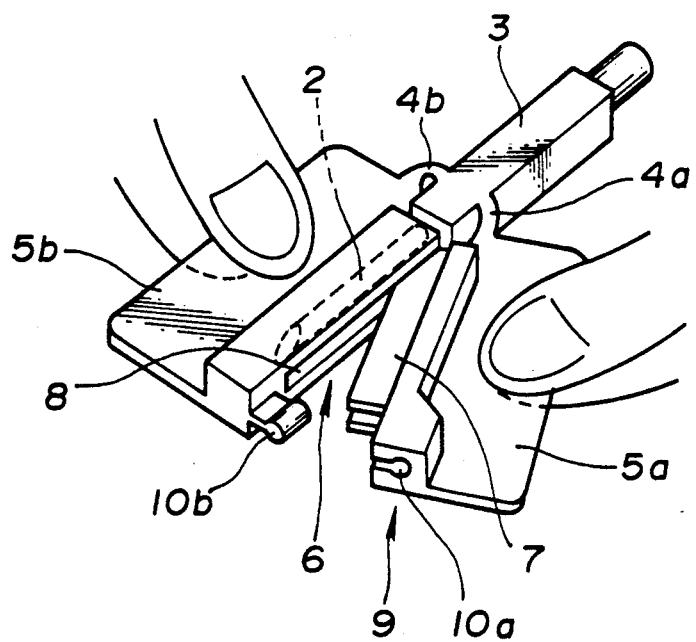
FIG. 2 is a perspective view of the first embodiment in the process of covering the needle.
Figure 3:
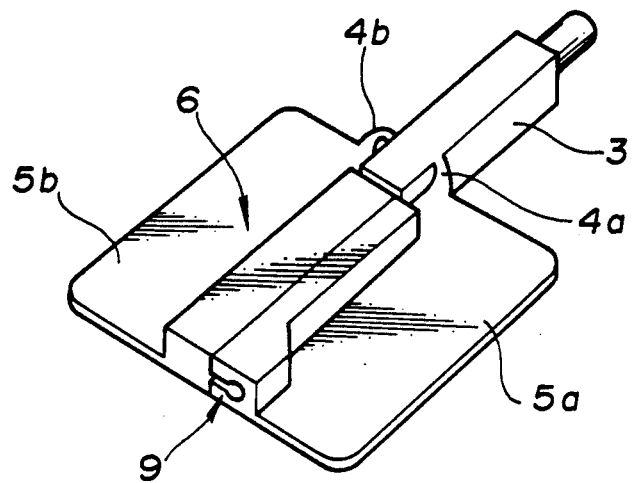
FIG. 3 is a perspective view of the first embodiment in completion of covering the needle.

For storage of the above embodiment, a user holds the wings 5a, 5b and folds the wings towards the needle 2 in order to form the sheath 6 to cover the needle, shown in FIG. 2, and couples the female and male parts 10a, 10b constituting the coupling means 9, to maintain the formation of the sheath or the bend of the arms, shown in FIG. 3.

For use, the user only has to undo the coupling means 9. The wings will swing back by restoring force of the arms 4a, 4b connecting the wings and the base 3, exposing the needle.

Figure 6:
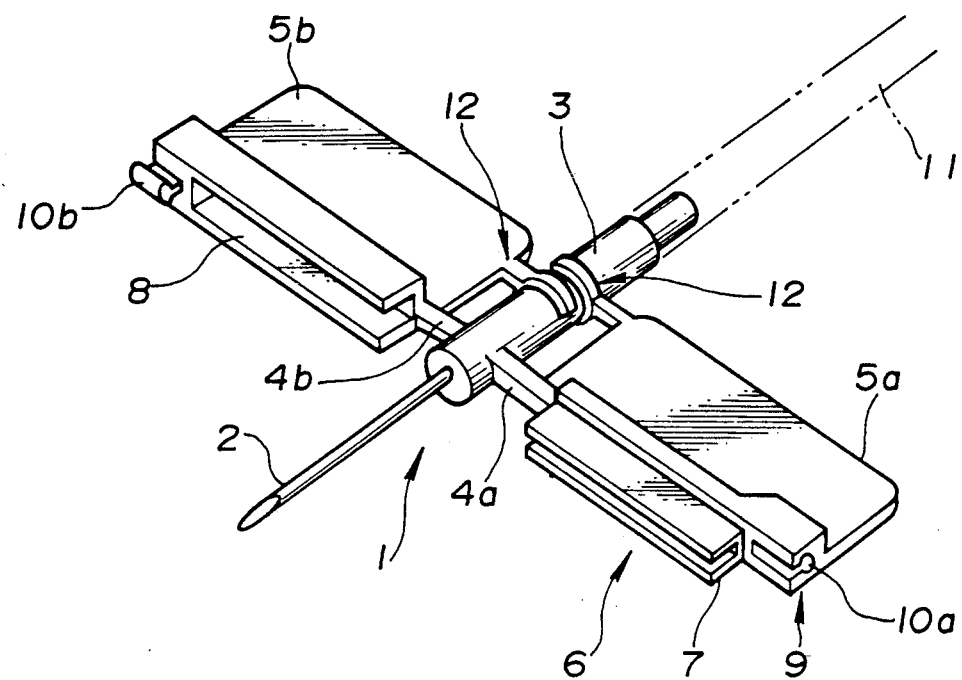
FIG. 6 is a perspective view of the second embodiment of the invention.
Figure 7:
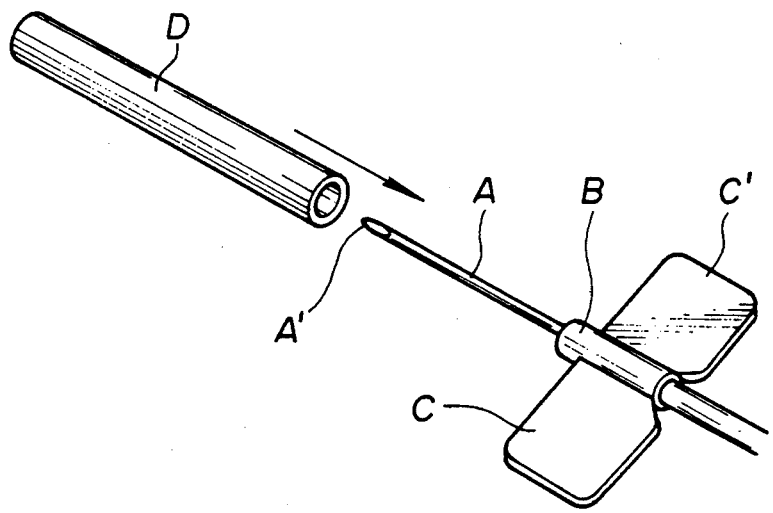
FIG. 7 is a perspective view of a related winged needle and sheath.

The wings 5a, 5b can be provided with engaging means 12 which releasably engages the base 3 as shown in FIG. 6. The engaging means 12 reinforces the rigidity of the unit, particularly when the wings 5a, 5b are folded up like a sandwich along the base 3. Thus the user can securely hold the needle by grasping the sandwiched wings when applying the needle 2 to a patient.

Although the base 3 is shaped like a cylinder and the engaging means 12 like C-rings in FIG. 6, the shapes can be made in any way if the structures fulfill the following conditions:

1. Engaging the wings with the base is easy;
2. The engagement holds when the wings are folded up; and
3. Disengaging is easy when the wings are folded in to cover the needle.

The wings themselves will form a sheath to cover the needle since the invention has the structure as described above. The structure enables a user to handle the invention from the base side without having his hand face the needle tip, significantly reducing the possibility of puncturing his hands or, consequently, of being infected with AIDS or hepatitis type B by way of the needle if the patient is a carrier.

What is claimed is:

1. A winged needle comprising:
   a needle;
   a base into which the needle is rooted;
   a pair of flat wings which flank both sides of said base, for providing flat surfaces with which said winged needle can be fastened to an arm of a patient;
   hinge means which allow said pair of wings to fold toward said needle;
   sheath-portions respectively integrated with said pair of flat wings which surround said needle on all sides when said pair of flat wings are folded toward said needle; and
   coupling means for coupling said pair of flat wings together with said sheath-portions when said pair of wings are folded to maintain said needle surrounded by said sheath portions.

2. A winged needle as defined in claim 1 wherein said sheath-portions includes:
   a ditched projection which is formed on one of two meeting edges of the wings and makes a three-sided cover for the needle; and
   a lipped section which is formed on the other meeting edge and accepts said ditched projection.

3. A winged needle as defined in claim 1 wherein said coupling means includes female and male parts which couple by elastic deformation.

4. A winged needle as defined in claim 1 including engaging means which engages said base and said wings when said wings are not folded towards said needle.

5. A winged needle according to claim 1, wherein all of said base, said pair of flat wings, said hinge means, said sheath-portions and said coupling means are formed from a flexible elastic material as a unitary member.

* * * * *